United States Patent [19]

Ramos-Caldera

[11] 4,134,647

[45] Jan. 16, 1979

[54] CONTACT LENS FOR EXAMINING THE INTERIOR OF THE EYE

[76] Inventor: Arturo J. Ramos-Caldera, Calle "C", Residencias Guaribe Apartamento 6-B Santa Rosa de Lima, Caracas, Venezuela

[21] Appl. No.: 780,079

[22] Filed: Mar. 22, 1977

[51] Int. Cl.² .............................................. A61B 3/10
[52] U.S. Cl. .......................................... 351/6; 351/39
[58] Field of Search ........................... 351/6, 7, 16, 39

[56] References Cited

U.S. PATENT DOCUMENTS

| 3,820,879 | 6/1974 | Frisen | 351/6 X |
| 3,944,341 | 3/1976 | Pomerantzeff | 351/6 X |
| 4,007,980 | 2/1977 | Bracher et al. | 351/6 |
| 4,033,679 | 7/1977 | Sussman | 351/6 X |

FOREIGN PATENT DOCUMENTS 466329 10/1951 Italy ............................................. 351/6

Primary Examiner—Paul A. Sacher
Attorney, Agent, or Firm—Phillips, Moore, Weissenberger, Lempio & Majestic

[57] ABSTRACT

The inner walls of the eye, i.e., the fundus, are examined in panorama with an optical lens comprising a truncate paraboloidal mirror and a corneal contact objective lens. While held in contact with the cornea, the fundus is observed by projecting a light beam into the eye through the lens and viewing the interior eye with a microscope, e.g., a standard slit lamp instrument.

5 Claims, 2 Drawing Figures

CONTACT LENS FOR EXAMINING THE INTERIOR OF THE EYE

BACKGROUND OF THE DISCLOSURE

In standard examinations of the eye's vitreous humor and fundus structures, an ophthalmoscope and/or a slit lamp with standard lenses are universally used. However, when a more complete and thorough examination of interesting regions of the fundus is desired, contact lenses are often used. Such lenses help in clarifying uncertain diagnosis and often permit viewing of lateral areas of the fundus that are sometimes inaccessible to direct ophthalmoscopic examination. The most commonly used are known as Goldmann's lenses, after their originator, and comprise a central lens and one or more plane mirrors incorporated into their structure. The mirror surfaces are inclined at various angles to the anterior-posterior axis and permit examination of the lateral fundus surfaces and the angle of the anterior chamber.

The portion of the fundus available for observation (with exclusion of the posterior pole which is examined with the central lens) is dependent upon the angular orientation of the plane mirror surface to the anterior-posterior axis of the eyeball, and it is therefore necessary to supply plane mirrors in several configurations inclined at various angles to the central lens axis. In some versions, a multiple number of mirror surfaces are incorporated into a single lens. However, in all such lenses, the plane mirror is capable of viewing only a limited area of the fundus according to the orientation of the mirror, and the area upon which it is focused. To complete a panorama observation of the fundus, it is therefore necessary to progressively rotate the contact lens through a 360° arc while observing the fundus, and to successively use the other angled mirror surfaces with the same procedure. It will be apparent that such examination is extremely tiresome and time consuming both for the patient and physician.

BRIEF SUMMARY OF THE INVENTION

The present invention relates to a contact lens for observing the fundus of the eye and especially the lateral surfaces thereof. More specifically, the invention incorporates a truncated paraboloidal mirrored surface with a generally conically shaped housing to afford a panoramic view of the fundus. Such lens is held in contact with the cornea and a light beam, e.g., a beam from a slit lamp, is directed into the eye through the lens to illuminate the fundus. Any desired portion of the fundus not directly observable by a central lens may then be viewed by directing a microscope to any desired area of the paraboloidal mirror, which reflects the fundus thereon.

The lens itself comprises an anterior surface, and an objective surface shaped to conform with the external corneal surface. A truncate paraboloidal lens portion connects the anterior surface and the objective surface or central portion of the lens. The lateral surface of the paraboloidal lens is silvered or polished to produce a paraboloidal mirror. An external housing, preferably conical in shape, encloses the paraboloidal lens and protects the mirrored surface.

It is therefore an object of the invention to provide a contact lens for viewing the fundus of the eye.

It is another object of the invention to provide a lens for contacting the external corneal surface to afford viewing of any desired portion of the fundus.

It is another object of the invention to provide a contact lens through which all portions of the fundus may be viewed without the necessity for rotating the lens or using a series of lenses.

It is still another object of the invention to provide a contact lens for viewing the fundus of the eye wherein a paraboloidal mirrored surface is utilized.

Other objects and advantages will become apparent from a review of the following description and appended claims along with the accompanying drawing wherein:

FIG. 1 is a perspective, partly cut-away view of a contact lens of the invention; and FIG. 2 is a vertical sectional view of a contact lens of the invention in position on the eye.

DETAILED DESCRIPTION OF THE INVENTION

Figure 1:
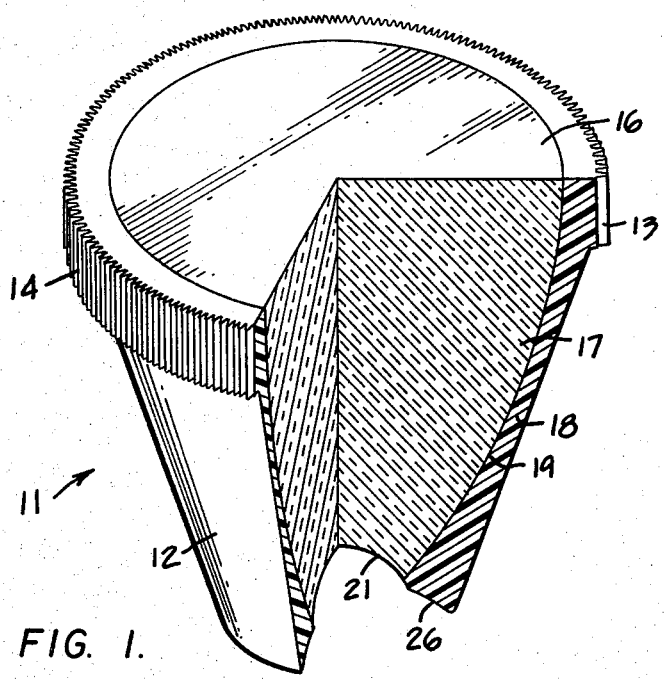

In a preferred embodiment, and with particular reference to FIG. 1, the lens 11 of the invention comprises a generally conical shaped housing 12 for enclosing the lens therein. The upper lateral portion of housing 11 comprises a ring 13 that includes serrations 14 therearound to facilitate handling and holding of the lens.

An interior surface 16 encloses the upper end of housing 12. Anterior surface 16 may also comprise the upper surface of a paraboloidal lens 17 that is enclosed by housing 12. Lens 17 is somewhat smaller in cross-section than housing 12 and is secured therein by an opaque layer 18 that comprises the interior of housing 11. Layer 18 may be fabricated from a mastic or other polymeric material that is firmly adhered both to housing 11 and lens 17 to rigidly secure and position lens 17 therein.

The lateral exterior surface of lens 17 is silvered or polished to provide a mirrored surface 19 that is reflective into the interior of lens 17. The objective surface 21 of paraboloidal lens 17 is truncated and shaped in a generally spherical configuration, concave inwardly. Surface 21 is specifically shaped to conform to the average corneal external surface 22 of an eyeball 24. Surrounding the objective surface 21 of lens 17, layer 18 has a surface 26 shaped to conform to the cornea periphery and the sclercorneal sulcus to achieve a close fit to the pericorneal portions of the eye.

Figure 2:
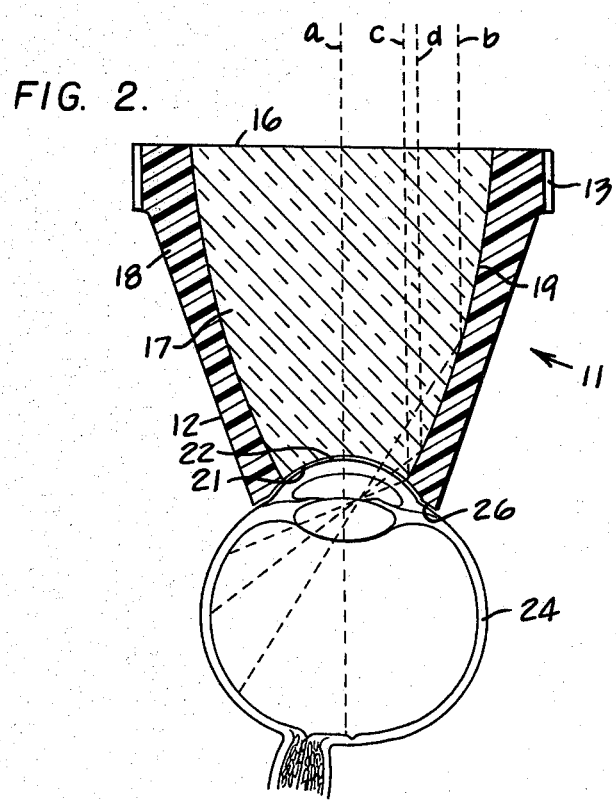

As illustrated in FIG. 2, lens 11 is used by holding the central portion of the lens against the cornea. The eyeball is first anesthetized and a buffer fluid such as methyl cellulose is introduced between the lens and the corneal surface. The retina is observed axially through the lens 11 and the eyeball 24 is indicated by the sight line "a". The lateral portions of the fundus may be observed by focusing, with the microscope on different sections of the paraboloidal mirror surface 19 as indicated by sight line "b"; portions of the fundus slightly off the posterior pole in the eye are observed by focusing on the upper portions of mirror surface 19; while increasingly lateral fundus portions are observed by focusing on progressively lower and more angular regions of the mirrored surface 19, as indicated by sight lines "c" and "d".

It will be apparent, however, that the fundus can be observed by merely focusing on any desired portion of the reflective paraboloidal surface 19, or through central lens 21. By such means an entire panorama of the fundus can be obtained almost without interruption.

What is claimed is:

1. A contact lens for observing the fundus of the eye comprising a truncate paraboloidal mirror and a transparent objective surface shaped for close contact with the cornea of the eye, and wherein said objective surface defines the truncate end of said paraboloidal mirror.

2. The contact lens of claim 1 wherein said paraboloidal mirror comprises the lateral surface of a truncate paraboloidal lens.

3. A contact lens for observing the fundus of the eye comprising a generally conical housing, a truncate paraboloidal lens enclosed within said housing, an inwardly reflecting mirror on the lateral surfaces of said paraboloidal lens, a concave cornea shaped objective surface comprising the truncate end of said paraboloidal lens, and means for rigidly retaining said paraboloidal lens in said housing.

4. A method for examining the fundus of the eye comprising contacting the cornea of the eye with a truncate paraboloidal lens having an inwardly reflecting mirrored lateral surface, and wherein the truncate portion of said lens is maintained in proximity to said cornea, directing a light beam into the eye and observing the fundus by viewing the reflection thereof in selected areas of said mirrored surface.

5. The method of claim 5 wherein the fundus reflection is viewed with a microscope.

* * * * *